United States Patent
Kern

[11] Patent Number: 5,888,989
[45] Date of Patent: Mar. 30, 1999

[54] SYNERGISTIC COMPOSITIONS FOR CONTROLLING INSECTS AND ACARINA

[75] Inventor: Manfred Kern, Lörzweiler, Germany

[73] Assignee: Hoechst Aktiengesellschaft, Frankfurt, Germany

[21] Appl. No.: 575,688

[22] Filed: Dec. 19, 1995

[30] Foreign Application Priority Data

Dec. 21, 1994 [DE] Germany ............... 44 45 732.4

[51] Int. Cl.$^6$ .................. A01N 31/14; A01N 55/00; A01N 63/00; A01N 63/04
[52] U.S. Cl. .................. 514/63; 424/93.5; 514/721
[58] Field of Search .................. 514/63, 721; 424/93.5

[56] References Cited

U.S. PATENT DOCUMENTS

| | | | |
|---|---|---|---|
| 4,570,005 | 2/1986 | Nakatani et al. | 549/435 |
| 4,751,082 | 6/1988 | Schaerffenberg et al. | 424/93 |
| 4,883,789 | 11/1989 | Sieburth | 514/63 |

FOREIGN PATENT DOCUMENTS

| | | |
|---|---|---|
| 2086351 | 7/1993 | Canada . |
| 0627165 | 12/1994 | European Pat. Off. . |

OTHER PUBLICATIONS

Journal of Economic Entamology (1989) Feb. No. 1, by Anderson et al. entitled "Colorado Potato Beetle (Coleoptera: Chrysomelidae): Effects of Combinations of *Beauveria bassiana* with Insecticides".
Soper et al., *Environmental Entomology* 3:560–562 (1974).
Ramiro et al., *Biologico* 53:7–23 (1987).

*Primary Examiner*—Allen J. Robinson
*Attorney, Agent, or Firm*—Frommer Lawrence & Haug

[57] ABSTRACT

The invention relates to insecticidal and acaricidal compositions of silafluofen and at least one entomopathogenic fungus, such as, for example, *Beauveria bassiana*.

15 Claims, No Drawings

SYNERGISTIC COMPOSITIONS FOR CONTROLLING INSECTS AND ACARINA

Frequently, the potency of biological pesticides is insufficient to protect crops of useful plants adequately against pests. This is why, to date, preference has been given to chemical insecticides. Integrated crop protection is intended to minimize the use of chemicals without simultaneously having to accept reduced yields.

The publication of Soper et al. (1974, Environmental Entomology, 3, 560–562) discloses that the growth of entomopathogenic fungi is inhibited by the simultaneous use of insecticides. Even though this depends on the type and the amount of the agent used, it can be seen from the data that there is a powerful adverse effect on fungal growth. Filho et al. (1987, Biologico, 53, 7–12, 69–70) also report that the growth of *Beauveria bassiana* is inhibited by a range of insecticides. EP 0 668 722 only discloses that the fungus *Beauveria bassiana* can be employed in combination with endosulfan.

Surprisingly, biological experiments have now identified insecticides with a completely different structure which, when used jointly with spores or particles of an entomopathogenic fungus, show an exceedingly good activity against a broad spectrum of a range of insects and Acarina.

The present invention relates to insecticidal and acaricidal compositions which comprise an effective amount of at least one insecticidal composition selected from the group of the parapyrethroids, the group of the nitromethylenes, the group of the carbamates and the group of the phenylpyrazoles.

The invention particularly relates to the following insecticides as components in mixtures:

1 ) parapyrethroids (non-ester pyrethroids), such as, for example, silafluofen (4-ethoxyphenyl-[3-(4-fluoro-3-phenoxyphenyl)propyl]dimethylsilane, formula I, component A1)

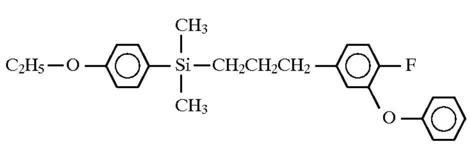

(I)

and etofenprox (2-(4-ethoxyphenyl)-2-methylpropyl 3-phenoxybenzyl ether, formula II, component A2), 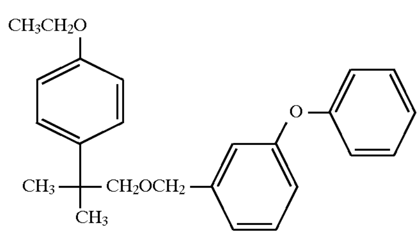 (II)

2) nitromethylenes, such as, for example, imidacloprid (1-(6-chloro-3-pyridylmethyl)-N-nitroimidazolidin-2-ylideneamine, formula III, component A3), 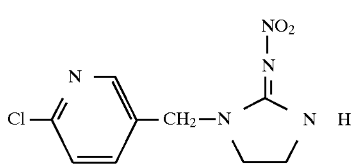 (III)

NI25 ((E)-$N^1$-[(6-chloro-3-pyridyl)methyl]-$N^2$-cyano-$N^1$-methylacetamidine, formula IV, component A4), 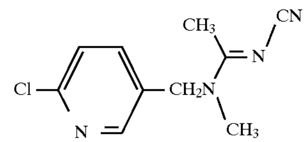 (IV)

and nitenpyram ((E)-N-(6-chloro-3-pyridylmethyl)-N-ethyl-N'-methyl-2-nitrovinylidenediamine, formula (V), component A5), 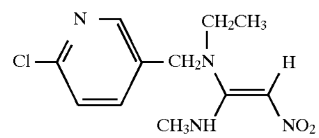 (V)

3) carbamates, such as, for example, fenoxycarb (ethyl 2-(4-phenoxyphenoxy)ethylcarbamate, formula VI, component A6)

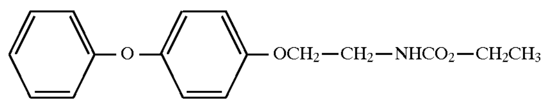

(VI)

4) phenylpyrazoles, such as, for example, fipronil ((+)-5-amino-1-(2,6-dichloro-α,α,α-trifluoro-p-tolyl)-4-trifluoromethylsulfinylpyrazole-3-carbonitrile, formula VII, component A7).

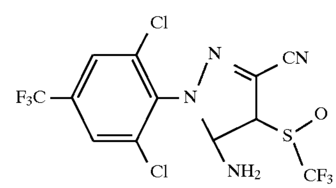

(VII)

in combination with at least one entomopathogenic fungus (component B).

The abovementioned compounds are all known from the literature ("Pesticide Manual", 10th Edition, Brit. Crop Prot. Council, 1994) and, commercially available.

A particularly interesting action against insects is shown by a mixture of silafluofen and fungi of the genera Acremonium, Acanthomyces, Aschersonia, Aspergillus, Beauveria, Culicinomyces, Engyodontium, Funicularis, Fusarium, Gibellula, Hirsutella, Hymenstilbe, Metarhizium, Nomuraea, Paecilomyces, Paraisaria, Pleurodesmopora, Polycephalomyces, Pseudogibellula, Sorosporella, Sporothrix, "Stilbella", Tetracrium, Tetranacrium, Tilachlidium, Tolypocladium, and Verticillium. All these genera are assigned to the section of the Deuteromycota (Samson et al., "Atlas of Entomopathogenic Fungi, 1988, Springer Verlag).

Fungi of the genera Hirsutella, Verticillium, Metarhizium, Beauveria, Paecilomyces and Nomuraea are of particular interest.

The mycoinsecticide constituent can be present in a variety of forms: as conidiospores, as blastospores, as bundles of hyphae, as hyphal fragments or as a mixture of two or more of the abovementioned forms.

In particular, the invention relates to insecticidal and acaricidal compositions which comprise the fungus *Beauveria bassiana* or *Metarhizium anisoplii.*

The fungus *Beauveria bassiana* has been described by Bassi, A. (1836, C. R. Acad. Sci. Paris 2, 434 to 436), Domsch, V. H. et al. (190, Compendium of Soil Fungi 1, 136 to 139) and Samson, R. A. et al. (1988, Atlas of Entomopathogenic Fungi, Springer-Verlag, Berlin) and is available from Mycotech (Butte, Mont., USA), from Hoechst Schering AgrEvo GmbH and from Troy Sciences (formerly Fermone Corp.) (Phoenix, Ariz., USA). In the text which follows, the term active substance is also used for each of the two components A or B.

The mixing ratios of the two components can vary within wide limits. They depend, in particular, on the component employed in the mixture, on the development stage of the pests and on the climatic conditions.

The invention also relates to compositions which comprise the two components A and B in addition to suitable formulation auxiliaries.

The active substance combinations according to the invention can exist not only as mixed formulations of the two components which are then diluted with water in the customary manner or applied as granules, but also in the form of so-called tank mixes by jointly diluting the components, which are formulated separately, with water.

Based on these formulations, it is also possible to prepare combinations with other pesticidally active substances, such as selective herbicides and specific fungicides or insecticides, and also fertilizers and/or growth regulators, for example in the form of a readymix or a tank mix.

The components can be formulated in a variety of ways, depending on the biological and/or chemico-physical parameters which prevail. Suitable formulation options are, for example: yeast formulations, starch formulations, wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed treatment products, granules for soil application or spreading, or water-dispersible granules (WG), ULV formulations, microcapsules or baits (substrates).

Oil-in-water and water-in-oil emulsions, wettable powders or granules are of particular interest.

These individual formulation types are known in principle and are described, for example, in: Winnacker-Küchler, "Chemische Technologie" [Chemical Technology], Vol. 7, C. Hauser Verlag Munich, 4th Ed. 1986; van Valkenburg, "Pesticide Formulations", Marcel Dekker N. Y., 2nd Edition 1972–73; K. Martens, "Spray Drying Handbook", 3rd Edition, G. Goodwin Ltd. London.

The formulation auxiliaries required, such as inert materials, surfactants, solvents and other additives, are also known and are described, for example, in: Watkins "Handbook of Insecticide Dust Diluents and Carriers", 2nd Edition, Darland Books, Caldwell N. J.; H. v. Olphen, "Introduction to Clay Colloid Chemistry", 2nd Edition, J. Wiley & Sons, N. Y., Marsden, "Solvents Guide", 2nd Edition, Interscience, N. Y. 1950; McCutcheon's, "Detergents and Emulsifiers Annual", MC Publ. Corp., Ridgewood N. J.; Sisley and Wood, "Encyclopedia of Surface Active Agents", Chem. Publ. Co. Inc., N. Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Vol. 7, C. Hauser Verlag Munich, 4th Ed. 1986.

Wettable powders are preparations which are uniformly dispersible in water and which, besides the active substance, also comprise wetting agents, for example polyoxyethylated alkylphenols, polyoxyethylated fatty alcohols or fatty amines, alkane sulfonates or alkylbenzene sulfonates, and dispersants, for example sodium lignosulfonate, sodium 2,2'-dinaphthylmethane-6,6'-disulfonate, sodium dibutyl-naphthalene sulfonate, or else sodium oleoylmethyltaurinate, in addition to a diluent or inert substance.

Emulsifiable concentrates are prepared by dissolving the active substance in an organic solvent, for example butanol, cyclohexanone, dimethylformamide, xylene, or else higher-boiling aromatic compounds or hydrocarbons, with the addition of one or more emulsifiers. Examples of emulsifiers which can be used are: calcium alkylarylsulfonates, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts can be obtained by grinding the active substance with finely divided solid substances, for example talc, natural clays, such as kaolin, bentonite and pyrophyllite, or diatomaceous earth.

Granules can be produced either by spraying the active substance onto adsorptive, granulated inert material or by applying active substance concentrates to the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, the agrochemical preparations comprise 0.0001 to 99 percent by weight, in particular between 0.0005 and 95%, particularly preferably between 2 and 90%, of the two components A and B. The low concentrations i.e. 0.0001 to 2% are advantageously used for controlling undesirable social insects, as this has been suggested in P 44 03 062.2.

The concentrations of the active substances A and B may differ in the formulations.

The concentration of active substance in wettable powders is, for example, about 10 to 90% by weight; the remainder to 100% by weight is composed of conventional formulation components. In the case of emulsifiable concentrates, the concentration of active substance can be about 1 to 90% by weight, preferably 5 to 80% by weight. Formulations in the form of dusts comprise about 1 to 30% by weight, preferably 5 to 20% by weight, of active substance, sprayable solutions about 0.05 to 80% by weight, preferably 2 to 50% by weight, of active substance. In the case of granules, for example water-dispersible granules, the active substance content depends partly on whether the active compound is in liquid or solid form and on which granulation auxiliaries and fillers are used. As a rule, water-dispersible granules comprise between 1 and 95% by weight, granules for spreading between 1 and 50%, preferably between 2 and 25%. Baits have an active substance content of between 0.0001 and 10% as regards component 1.

The use concentration can vary between 0.1 ppm ($\hat{=}$ 0.0001 g/l) and 10,000 ppm ($\hat{=}$ 10 g/l), preferably between 0.5 and 5,000 ppm, particularly preferably between 5 and 1,000 ppm.

A mixture which has proved effective comprises the insecticidal component and mycoinsecticidal component used in such a ratio that the content of component A amounts to between 0.01 and 50%, preferably 0.1 to 50%, and the amount of mycoinsecticide to $10^2$ to $10^{15}$ spores, preferably $10^5$ to $10^{12}$ spores, or between 0.01 g and 1,000 g of formulated substance.

In addition, the active substance formulations mentioned comprise, if appropriate, the adhesives, wetting agents, dispersants, emulsifiers, penetrants, solvents, fillers or carriers which are conventional in each case.

For use, the formulations, which are present in commercially available form, are diluted, if appropriate, in a customary manner, for example using water in the case of wettable powders, emulsifiable concentrates, dispersions and water-dispersible granules. Preparations in the form of dusts or granules for soil application or spreading and sprayable solutions are usually not further diluted with other inert substances before use.

The component B can be formulated for example as described by Prior, C. et al. in the Journal of Invertebrate Pathology 52, 66 to 72 (1988). Preferably, component B is formulated as proposed in P 44 04 702.9

The application rate of the mixture required varies with the external conditions, such as, for example, temperature, humidity and the like. It also depends on the particular field of application and on the plant to be treated and can therefore vary within wide limits. It is between 1 g/ha and 200 g/ha, preferably between 20 g/ha and 100 g/ha, particularly preferably between 40 g/ha and 80 g/ha in the case of component A (for example silafluofen).

In the case of the entomopathogenic fungus, it is between 10 g of conidia/ha and 1,000 g of conidia/ha, preferably between 20 g of conidia/ha and 400 g/ha.

$10^8$ to $10^{10}$ g of conidia of an entomopathogenic fungus are approximately 1 g.

The two components A and B can be applied simultaneously or in succession. It makes sense to carry out the second application after the first application has dried on the plant so as to avoid undesirable washing off of the first component.

The combination of component (A) and the entomopathogenic fungi (B) is well tolerated by plants, has a favorable toxicity to warm-blooded species and is suitable for controlling animal pests in agriculture, in particular insects and arachnids.

The synergistic mixture of the two components is active against normally sensitive and resistant species and against certain stages of development. The compositions according to the invention have an outstanding insecticidal activity against a broad spectrum of economically important pests. Some representatives of pests which can be controlled by the compositions according to the invention may be mentioned individually by way of example, but this is not intended as a limitation to certain species.

From the order of the Isopoda, for example, *Oniscus asellus*, *Armadium vulgare* and *Porcellio scaber*. From the order of the Diplopoda, for example, *Blaniulus guttulatus*. From the order of the Chilopoda, for example, *Geophilus carpophagus* and *Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis*, *Periplaneta americana*, *Leucophaea maderae*, *Blattella germanica*, *Acheta domesticus*, *Gryllotalpa spp.*, *Locusta migratoria migratorioides*, *Melanoplus differentialis* and *Schistocerca gregaria*. From the order of the Dermaptera, for example, *Forficula auricularia*. From the order of the Anoplura, for example, *Phylloxera vastatrix*, *Pemphigus spp.*, *Pediculus humanus corporis*, *Haematopinus spp.* and *Linognathus spp.*

From the order of the Mallophaga, for example, *Trichodectes spp.* and *Damalinea spp.* From the order of the Thysanoptera, for example, *Hercinothrips femoralis* and *Thrips tabaci*. From the order of the Heteroptera, for example, *Eurygaster spp.*, *Dysdercus intermedius*, *Piesma quadrata*, *Cimex lectularius*, *Rhodnius prolixus* and *Triatoma spp.* From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, *Myzus spp.*, *Phorodon humuli*, *Rhopalosiphum padi*, *Empoasca spp.*, *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus spp.* and *Psylla spp.*

From the order of the Lepidoptera, for example, *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, *Lymantria spp.*, *Bucculatrix thurberiella*, *Phyllocnistis citrella*, *Agrotis spp.*, *Euxoa spp.*, *Feltia spp.*, *Earias insulana*, *Heliothis spp.*, *Laphygma exigua*, *Mamestra brassicae*, *Panolis flammea*, *Prodenia litura*, *Spodoptera spp.*, *Trichoplusia ni*, *Carpocapsa pomonella*, *Perileucoptera coffeella*, *Pieris spp.*, *Chilo spp.*, *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima*, *Tortrix viridana*.

From the order of the Coleoptera, for example, *Anobium punctatum*, *Hypothemenus hampei*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica spp.*, *Psylliodes chrysocephala*, *Epilachna varivestis*, *Atomaria spp.*, *Oryzaephilus surinamensis*, *Anthonomus spp.*, *Sitophilus spp.*, *Otiorrhynchus sulcatus*, *Cosmopolites sordidus*, *Ceuthorrhynchus assimilis*, *Hypera postica*, *Dermestes spp.*, *Trogoderma spp.*, *Anthrenus spp.*, *Attagenus spp.*, *Lyctus spp.*, *Meligethes aeneus*, *Ptinus spp.*, *Niptus hololeucus*, *Gibbium psylloides*, *Tribolium spp.*, *Tenebrio molitor*, *Agriotes spp.*, *Conoderus spp.*, *Melolontha melolontha*, *Amphimallon solstitialis* and *Costelytra zealandica*.

From the order of the Hymenoptera, for example, *Diprion spp.*, *Hoplocampa spp.*, *Lasius spp.*, *Monomorium pharaonis* and *Vespa spp.*

From the order of the Isoptera, the families Mastotermitidae, Kalotermitidae, Hodotermitidae (in particular Hodotermitinae, Termopsinae), Rhonotermitidae (in particular Coptotermitinae, Heterotermitinae, Psammotermitinae), Termitidae (in particular Macrotermitinae, Nasutitermitinae, Termitinae), for example Mastotermes sp., such as *Mastrotermes darwiniensis*, Cryptotermes sp., Incistitermes sp., Kalotermes sp., such as *Kalotermes flavicollis*, Marginitermes sp., Anaconthotermes sp., Zootermopsis sp., Coptotermes sp., such as *Coptotermes formosanus*, Heterotermes sp., Psammotermes sp., Prorhinotermes sp., Schedorhinotermes sp., Allodontermes sp., Nasutitermes sp., Termes sp., Amitermes sp., Globitermes sp., Microcerotermes sp., *Oniscus asellus*, *Armadium vulgare*, *Porcellio scaber*, Reticulitermes sp., such as *Reticulitermes flavipes*, *Reticulitermes lucifugus*.

The active substance combinations according to the invention, especially Silafluofen and Fipronil respectively in combination with *Beauveria bassiana*, are particularly advantageous for controlling termites from the family Kalotermitidae, for example *Cryptotermes cubioceps*, *Kalotermes spp.*, from the family Rhinotermitidae, for example, *Coptotermes formosus*, *Heteretermes spp.*, from the family Termitidae, for example, *Nasutitermes spp.*, or the family Mastotermitidae, for example *Mastotermes darwiniensis*.

From the family of the Formicidae, for example *Atta cephalotes, Lasius niger, Lasius brunneus, Componotus ligniperda, Monomorium pharaonis, Solenopsis geminata, Monomorium minimum, Iridomyres humilis,* Dorylus sp., Exition sp.

From the super-family of the Vespoidea, for example *Vespa germanica, Vespa vulgaris, Vespa media, Vespa saxonica, Vespa crabro, Vespula macalata, Polistes nympha, Vespa orintalis, Vespa mandarinia, Vespa velutina.*

From the super-family of the Apoidea, the so-called killer bee may be mentioned.

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hypobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp.* From the order of the Arachnida, for example, *Scorpio maurus* and *Latrodectus mactans*. From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The combination according to the invention, of silafluofen and the entomopathogenic fungi is particularly suitable for controlling sensitive and resistant *Heliothis spp., Anthonomus spp., Hypothememus hampei, Spodoptera spp., Nephotettix spp., Nilaparvata lugens, Trichoplusia spp., Leptinotarsa decemlineata* and other feeding (termites, ants) and sucking insects, such as whitefly, or spider mites.

The active substance combinations according to the invention allow an insecticidal and acaricidal activity to be achieved which exceeds what is to be expected on the basis of the activity of the individual components. These increases in activity allow the application rates of the individual active substances to be reduced considerably. The combination of the active substances can also improve their long-term activity or cause an acceleration of the rate of activity. Such properties are of considerable advantage to the user for controlling insects in practice. They allow insects to be controlled more economically and more rapidly, with less labor and over a prolonged period, which means that better yields can be harvested in a population of crop plants.

A further increase in activity can be achieved by using so-called feeding attractants or phagostimulants, such as, for example, Konsume (from Pharmone), ATPlus, yeast, starch, Stirrup (from Atochem, North America Inc., USA) and Coax.

Even though the compositions according to the invention have an outstanding insecticidal and acaricidal activity, the crop plant is not harmed at all. This is why the compositions are particularly suitable in cotton, soya bean and rice crops. Very particularly advantageous is their use in rice and tea crops, because the climatic conditions are particularly advantageous for both products. They are also suitable for controlling pests in coffee, fruit and vegetable production, or else in viticulture.

The following examples are intended to illustrate the invention without imposing any restriction:

A. BIOLOGICAL EXAMPLES

In all cases, a differentiation was made between the calculated and the found degree of effectiveness of the combinations.

If the actual damage exceeds the damage expected by way of calculation, then the activity of the combination is superadditive, i.e. there is a synergistic effect. The active substance combinations according to the invention have an insecticidal activity which exceeds that to be expected on the basis of the observed activities of the individual components when used by themselves. This means that the active substance combinations are synergistic.

Example 1

*Spodoptera littoralis* in Combination With Silafluofen

Pyrethroid-resistant larvae of the Egyptian cotton leafworm (*Spodoptera littoralis*, L 3) together with suitable feed were sprayed with the active substances or mixture of these. The effect of the individual components and of the mixtures of the individual components was assessed 6 days after keeping the test material at 25° C. and a relative atmospheric humidity of 80%.

| Active substance/component | Active substance in ppm | % mortality |
|---|---|---|
| Silafluofen (A1) | 125 | 100 |
|  | 63 | 100 |
|  | 31 | 30 |
|  | 16 | 10 |
|  | 8 | 0 |
| Beauveria bassiana (B) (Natrualis-L) | $2.3 \cdot 10^{10}$ conidia/ha | 4 |

| (A1) + (B) | (A) + (B) | By calculation | In the experiment |
|---|---|---|---|
| (A1) + (B) | $125 + 2.3 \cdot 10^{10}$ | 100 | 100 |
|  | $63 + 2.3 \cdot 10^{10}$ | 100 | 100 |
|  | $31 + 2.3 \cdot 10^{10}$ | 34 | 80 |
|  | $16 + 2.3 \cdot 10^{10}$ | 14 | 80 |
|  | $8 + 2.3 \cdot 10^{10}$ | 4 | 10 |

Example 2

*Anthonomus grandis* Combination With Silafluofen

Adult specimens of the cotton boll weevil (*Anthonomus grandis*) together with suitable feed (synthetic feed) were sprayed with the active substances or their mixtures. The effect of the individual components and of the mixtures of the individual components was assessed 9 days after keeping the test material at 25° C. and a relative atmospheric humidity of 90%.

| Active substance/component | Active substance in ppm | % mortality |
|---|---|---|
| Silafluofen (A1) | 125 | 100 |
|  | 63 | 70 |
|  | 31 | 40 |
|  | 16 | 30 |
|  | 8 | 0 |
| Beauveria bassiana (B) (Natrualis-L) | $4.6 \cdot 10^{10}$ conidia/ha | 4 |

-continued

|  | (A) + (B) | By calculation | In the experiment |
|---|---|---|---|
| (A1) + (B) | 125 + 4.6 · 10¹⁰ | 100 | 100 |
|  | 63 + 4.6 · 10¹⁰ | 74 | 100 |
|  | 31 + 4.6 · 10¹⁰ | 44 | 60 |
|  | 16 + 4.6 · 10¹⁰ | 34 | 50 |
|  | 8 + 4.6 · 10¹⁰ | 4 | 10 |

Example 3

*Nilaparavata lugens* in Combination With Siaflufen

Larvae of the rice planthopper (*Nilaparvata lugens*) were placed on rice plants which had previously been immersed in aqueous solutions composed of active substances or of their mixtures. The effect of the individual components or of the mixtures of individual components was assessed 6 days after keeping the test material at 25° C. and a relative atmospheric humidity of 80%.

| Active substance/component | Active substance in ppm | % mortality |
|---|---|---|
| Silafluofen (A1) | 63 | 100 |
|  | 31 | 70 |
|  | 16 | 40 |
|  | 8 | 20 |
|  | 4 | 20 |
|  | 2 | 0 |
| Beauveria bassiana (B) (Natrualis-L) | 2.3 · 10¹⁰ conidia/ha | 28 |

|  | (A) + (B) | By calculation | In the experiment |
|---|---|---|---|
| (A1) + (B) | 63 + 2.3 · 10¹⁰ | 100 | 100 |
|  | 31 + 2.3 · 10¹⁰ | 98 | 100 |
|  | 16 + 2.3 · 10¹⁰ | 68 | 90 |
|  | 8 + 2.3 · 10¹⁰ | 48 | 80 |
|  | 4 + 2.3 · 10¹⁰ | 48 | 70 |
|  | 2 + 2.3 · 10¹⁰ | 28 | 50 |

Example 4

*Nilaparvata lugens* in Combination With Etofenprox

Larvae of the rice planthopper (*Nilaparvata lugens*) were placed on rice plants which had previously been immersed in aqueous solutions composed of active substances or of their mixtures. The effect of the individual components or of the mixtures of individual components was assessed 6 days after keeping the test material at 25° C. and a relative atmospheric humidity of 80%.

| Active substance/component | Active substance in ppm | % mortality |
|---|---|---|
| Etofenprox (A2) | 63 | 100 |
|  | 31 | 70 |
|  | 16 | 30 |
|  | 8 | 0 |
|  | 4 | 0 |
|  | 2 | 0 |
| Beauveria bassiana (B) (Natrualis-L) | 2.3 · 10¹⁰ conidia/ha | 28 |

|  | (A) + (B) | By calculation | In the experiment |
|---|---|---|---|
| (A2) + (B) | 63 + 2.3 · 10¹⁰ | 100 | 100 |
|  | 31 + 2.3 · 10¹⁰ | 98 | 100 |
|  | 16 + 2.3 · 10¹⁰ | 58 | 80 |
|  | 8 + 2.3 · 10¹⁰ | 28 | 80 |
|  | 4 + 2.3 · 10¹⁰ | 28 | 60 |
|  | 2 + 2.3 · 10¹⁰ | 28 | 40 |

Example 5

*Nilaparvata lugens* in Combination With Imidacloprid

Larvae of the rice planthopper (*Nilaparvata lugens*) were placed on rice plants which had previously been immersed in aqueous solutions composed of active substances or of their mixtures. The effect of the individual components or of the mixtures of individual components was assessed 6 days after keeping the test material at 25° C. and a relative atmospheric humidity of 80%.

| Active substance/component | Active substance in ppm | % mortality |
|---|---|---|
| Imidacloprid (A3) | 63 | 80 |
|  | 31 | 50 |
|  | 16 | 40 |
|  | 8 | 30 |
|  | 4 | 10 |
|  | 2 | 0 |
| Beauveria bassiana (B) (Natrualis-L) | 2.3 · 10¹⁰ conidia/ha | 28 |

|  | (A) + (B) | By calculation | In the experiment |
|---|---|---|---|
| (A4) + (B) | 63 + 2.3 · 10¹⁰ | 100 | 100 |
|  | 31 + 2.3 · 10¹⁰ | 78 | 100 |
|  | 16 + 2.3 · 10¹⁰ | 68 | 100 |
|  | 8 + 2.3 · 10¹⁰ | 58 | 90 |
|  | 4 + 2.3 · 10¹⁰ | 48 | 70 |
|  | 2 + 2.3 · 10¹⁰ | 28 | 70 |

Example 6

*Spodoptera littoralis* in Combination With NI25

Pryethroid-resistant larvae of the Egyptian cotton leafworm (*Spodoptera littoralis*, L 3) together with suitable feed were sprayed with the active substances or their mixtures. The effect of the individual components or of the mixtures of the individual components was assessed 6 days after keeping the test material at 25° C. and a relative atmospheric humidity of 80%.

| Active substance/component | Active substance in ppm | % mortality |
|---|---|---|
| NI-25 (A4) | 500 | 50 |
|  | 250 | 30 |
|  | 125 | 10 |
|  | 63 | 0 |

-continued

| | | |
|---|---|---|
| | 31 | 0 |
| | 16 | 0 |
| | 8 | 0 |
| Beauveria bassiana (B) (Natrualis-L) | $2.3 \cdot 10^{10}$ conidia/ha | 4 |

| | (A) + (B) | By calculation | In the experiment |
|---|---|---|---|
| (A4) + (B) | $500 + 2.3 \cdot 10^{10}$ | 54 | 100 |
| | $250 + 2.3 \cdot 10^{10}$ | 34 | 100 |
| | $125 + 2.3 \cdot 10^{10}$ | 14 | 80 |
| | $63 + 2.3 \cdot 10^{10}$ | 4 | 40 |
| | $31 + 2.3 \cdot 10^{10}$ | 4 | 10 |
| | $16 + 2.3 \cdot 10^{10}$ | 4 | 0 |
| | $8 + 2.3 \cdot 10^{10}$ | 4 | 0 |

Example 7

*Nilaparvata lugens* in Combination With Nitenpyram (TI-304)

Larvae of the rice planthopper (*Nilaparvata lugens*) were placed on rice plants which had previously been immersed in aqueous solutions composed of active substances or of their mixtures. The effect of the individual components or of the mixtures of individual components was assessed 6 days after keeping the test material at 25° C. and a relative atmospheric humidity of 80%.

| Active substance/component | Active substance in ppm | % mortality |
|---|---|---|
| Nitenpyram (TI-304) (A5) | 63 | 70 |
| | 31 | 30 |
| | 16 | 30 |
| | 8 | 0 |
| | 4 | 0 |
| | 2 | 0 |
| Beauveria bassiana (B) (Natrualis-L) | $2.3 \cdot 10^{10}$ conidia/ha | 28 |

| | (A) + (B) | By calculation | In the experiment |
|---|---|---|---|
| (A5) + (B) | $63 + 2.3 \cdot 10^{10}$ | 100 | 100 |
| | $31 + 2.3 \cdot 10^{10}$ | 58 | 100 |
| | $16 + 2.3 \cdot 10^{10}$ | 58 | 70 |
| | $8 + 2.3 \cdot 10^{10}$ | 28 | 50 |
| | $4 + 2.3 \cdot 10^{10}$ | 28 | 30 |
| | $2 + 2.3 \cdot 10^{10}$ | 28 | 30 |

Example 8

*Spodoptera littoralis* in Combination With Fenoxycarb

Pyrethroid-resistant larvae of the Egyptian cotton leafworm (Spodoptera littoralis, L 3) together with suitable feed were sprayed with the active substances or their mixtures. The effect of the individual components or of the mixtures of the individual components was assessed 6 days (10 days in the case of fenoxycarb) after keeping the test material at 25° C. and a relative atmospheric humidity of 80%.

| Active substance/component | Active substance in ppm | % mortality |
|---|---|---|
| Fenoxycarb (A6) | 250 | 100 |
| | 125 | 50 |
| | 63 | 30 |
| | 31 | 0 |
| | 16 | 0 |
| | 8 | 0 |
| Beauveria bassiana (B) (Natrualis-L) | $2.3 \cdot 10^{10}$ conidia/ha | 22 |

| | (A) + (B) | By calculation | In the experiment |
|---|---|---|---|
| (A6) + (B) | $500 + 2.3 \cdot 10^{10}$ | 100 | 100 |
| | $250 + 2.3 \cdot 10^{10}$ | 100 | 100 |
| | $125 + 2.3 \cdot 10^{10}$ | 72 | 100 |
| | $63 + 2.3 \cdot 10^{10}$ | 52 | 100 |
| | $31 + 2.3 \cdot 10^{10}$ | 22 | 70 |
| | $16 + 2.3 \cdot 10^{10}$ | 22 | 80 |
| | $8 + 2.3 \cdot 10^{10}$ | 22 | 60 |

Example 9

*Spodoptera littoralis* in Combination With Fipronil

Pyrethroid-resistant larvae of the Egyptian cotton leafworm (*Spodoptera littoralis*, L 3) together with suitable feed were sprayed with the active substances or their mixtures. The effect of the individual components or of the mixtures of the individual components was assessed 6 days after keeping the test material at 25° C. and a relative atmospheric humidity of 80%.

| Active substance/component | Active substance in ppm | % mortality |
|---|---|---|
| Fipronil (A7) | 125 | 40 |
| | 63 | 20 |
| | 31 | 0 |
| | 16 | 0 |
| | 8 | 0 |
| Beauveria bassiana (B) (Natrualis-L) | $2.3 \cdot 10^{10}$ conidia/ha | 4 |

| | (A) + (B) | By calculation | In the experiment |
|---|---|---|---|
| (A7) + (B) | $125 + 2.3 \cdot 10^{10}$ | 44 | 100 |
| | $63 + 2.3 \cdot 10^{10}$ | 24 | 80 |
| | $31 + 2.3 \cdot 10^{10}$ | 4 | 40 |
| | $16 + 2.3 \cdot 10^{10}$ | 4 | 30 |
| | $8 + 2.3 \cdot 10^{10}$ | 4 | 20 |

Example 10

*Anthomomus grandis* in Combination With Fipronil

Adult specimens of the cotton boll weevil (*Anthonomus grandis*) together with suitable feed (synthetic feed) were sprayed with active substances or their mixtures. The effect of the individual components and of the mixtures of the individual components was assessed 9 days after keeping the test material at 25° C. and a relative humidity of 90%.

| Active substance/component | Active substance in ppm | % mortality |
|---|---|---|
| Fipronil (A7) | 125 | 100 |
| | 63 | 100 |
| | 31 | 70 |
| | 16 | 40 |
| | 8 | 0 |
| | 4 | 0 |
| Beauveria bassiana (B) (Natrualis-L) | $4.6 \cdot 10^{10}$ conidia/ha | 40 |

| | (A) + (B) | By calculation | In the experiment |
|---|---|---|---|
| (A7) + (B) | $125 + 4.6 \cdot 10^{10}$ | 100 | 100 |
| | $63 + 4.6 \cdot 10^{10}$ | 100 | 100 |
| | $31 + 4.6 \cdot 10^{10}$ | 100 | 100 |
| | $16 + 4.6 \cdot 10^{10}$ | 80 | 100 |
| | $8 + 4.6 \cdot 10^{10}$ | 40 | 90 |
| | $4 + 4.6 \cdot 10^{10}$ | 40 | 80 |

I claim:

1. An insecticidal or acaricidal composition which comprises a synergistically insecticidal or acaricidal effective amounts of at least one parapyrethroid insecticide selected from the group consisting of silafluofen and etofenprox (component A) and at least one entomopathogenic fungus (component B).

2. The composition as claimed in claim 1, wherein the entomopathogenic fungus is selected from the group consisting of the genera Hirsutella, Verticillium. Metarhizium, Beauveria, Paecilomyces and Nomuraea.

3. The composition as claimed in claim 1, wherein the entomopathogenic fungus is *Beauveria bassiana.*

4. The composition as claimed in claim 1, wherein the entomopathogenic fungus is *Metarhizium anisoplii.*

5. The composition as claimed in claim 1, wherein the entomopathogenic fungus is composed of blastospores.

6. The composition as claimed in claim 1, wherein the entomopathogenic fungus is composed of mycelium or mycelial fragments.

7. The composition as claimed in claim 1, further comprising suitable formulation auxiliaries.

8. The composition as claimed in claim 1, which comprises 1 to 99% by weight of a composition as claimed in claim 1, in addition to customary formulation auxiliaries.

9. The composition as claimed in claim 1, wherein the composition is in the form of a conventional crop protection product formulation selected from the group consisting of wettable powders, emulsifiable concentrates, aqueous solutions, emulsions, sprayable solutions, oil-or-water-based dispersions, suspoemulsions, dusts, seed treatment products, granules for soil application or spreading, water-dispersible granules, ULV formulations, microcapsules and waxes.

10. The composition as claimed in claim 9, wherein the crop is cotton, soya bean, rice or coffee.

11. A synergistic insecticidal or acaricidal composition for controlling insects and acarids in crop, fruit, vegetable and other useful plants, which comprises about 0.01 to 50% by weight of at least one parapyrethroid insecticide selected from the group consisting of silafluofen and etofenprox (component A) and about $10^2$ to $10^5$ spores of at least one entomopathogenic fungus (component B).

12. A synergistic insecticidal or acaricidal composition for controlling insects and acarids in cotton, soybean, rice, tea, and coffee plants, which comprises 0.1 to 50% by weight of at least one parapyrethroid insecticide selected from the group consisting of silafluofen and etofenprox (component A) and about $10^5$ to $10^{12}$ spores of at least one entomopathogenic fungus (component B).

13. A method of controlling insect pests or acarids, which comprises applying a synergistically insecticidal or acaricidal effective amount of the composition as claimed in claim 17 to the insect pests or acarids or to the plants, areas or substrates infested with them.

14. A method of controlling insect pests or acarids, which comprise applying a synergistically insecticidal or acaricidal effective amount of the composition as claimed in claim 3 to the insect pests or acarids or to the plants, areas or substrates infested with them.

15. A method of controlling insect pests or acarids, which comprise applying a synergistically insecticidal or acaricidal effective amount of the composition as claimed in claim 11 to the insect pests or acarids or to the plants, areas or substrates infested with them.

* * * * *